(12) United States Patent
Chicchetti et al.

(10) Patent No.: US 9,456,799 B2
(45) Date of Patent: Oct. 4, 2016

(54) MODALITY WITH MULTICOMPUTER SYSTEM AND POWERING SEQUENCE THEREFOR

(71) Applicant: Virtual Imaging, Inc., Boca Raton, FL (US)

(72) Inventors: Peter M. Chicchetti, Coral Springs, FL (US); Carmine Pizzuto, Boca Raton, FL (US)

(73) Assignee: Virtual Imaging, Inc., Boca Raton, FL (US)

( * ) Notice: Subject to any disclaimer, the term of this patent is extended or adjusted under 35 U.S.C. 154(b) by 139 days.

(21) Appl. No.: 14/200,976

(22) Filed: Mar. 7, 2014

(65) Prior Publication Data

US 2014/0254769 A1    Sep. 11, 2014

Related U.S. Application Data

(60) Provisional application No. 61/775,358, filed on Mar. 8, 2013.

(51) Int. Cl.

| | |
|---|---|
| *G06F 1/32* | (2006.01) |
| *A61B 6/00* | (2006.01) |
| *G06F 19/00* | (2011.01) |
| *G06F 1/26* | (2006.01) |

(52) U.S. Cl.
CPC ............. *A61B 6/563* (2013.01); *A61B 6/4405* (2013.01); *A61B 6/54* (2013.01); *A61B 6/56* (2013.01); *G06F 19/3406* (2013.01); *G06F 1/26* (2013.01)

(58) Field of Classification Search
CPC ..................................................... A61B 6/563
USPC ........................................................ 713/300
See application file for complete search history.

(56) References Cited

U.S. PATENT DOCUMENTS

| | | | | |
|---|---|---|---|---|
| 5,680,536 A | * | 10/1997 | Tyuluman | G06F 15/7864 714/1 |
| 5,828,140 A | * | 10/1998 | Shih | G06F 1/30 307/18 |
| 6,557,170 B1 | * | 4/2003 | Wilder | G06F 3/023 345/168 |
| 6,661,123 B2 | | 12/2003 | Hsu | |
| 8,281,167 B2 | * | 10/2012 | Nakamura | B60W 50/04 180/65.1 |

(Continued)

OTHER PUBLICATIONS

Adams, "Microwulf: A Personal, portable Beowulf Cluster", Microwulf Design, Apr. 12, 2013, pp. 1-2, www.calvin.edu/~adams/research/microwulf/design/.

(Continued)

*Primary Examiner* — Thomas Lee
*Assistant Examiner* — Volvick Derose
(74) *Attorney, Agent, or Firm* — Canon U.S.A. Inc., IP Division

(57) ABSTRACT

An imaging modality includes a first computer, a second computer, a computer select circuit connected to a manually operable switch and configured to allow an operator to select whether to operate the first computer or the second computer by manually operating the manually operable switch, a single power supply unit configured to supply operating power to the first computer and the second computer; and a power control circuit connected to a power input of the first computer and connected to a power input of the second computer. The power control circuit outputs a trigger signal to activate or deactivate flow of power supply to the second computer in response to first computer receiving a turn ON or turn OFF input.

20 Claims, 11 Drawing Sheets

(56) References Cited

U.S. PATENT DOCUMENTS

| | | |
|---|---|---|
| 8,314,805 B2 | 11/2012 | Wang et al. |
| 2002/0004915 A1 | 1/2002 | Fung |
| 2007/0007824 A1 | 1/2007 | Chen et al. |
| 2009/0158057 A1 | 6/2009 | Begun et al. |
| 2009/0177901 A1* | 7/2009 | Chen ................. G06F 3/023 |
| | | 713/310 |
| 2009/0217064 A1* | 8/2009 | Terasawa ............ G06F 1/26 |
| | | 713/310 |
| 2009/0230781 A1 | 9/2009 | Hung et al. |
| 2009/0265412 A1 | 10/2009 | Hainzer |
| 2011/0018342 A1 | 1/2011 | Park et al. |
| 2012/0013186 A1 | 1/2012 | Sarti |
| 2012/0191990 A1* | 7/2012 | Hodge ............... G06F 11/3055 |
| | | 713/300 |
| 2012/0293017 A1* | 11/2012 | Lidsky ............... H02H 3/087 |
| | | 307/126 |
| 2013/0103934 A1* | 4/2013 | Hashioka ........... G06F 21/575 |
| | | 713/1 |

OTHER PUBLICATIONS

Bursky, et al. "Securing a Multicore, Dual OS, Wireless Medical Platform", Embedded Intel, Apr. 25, 2013; pp. 1-5.

* cited by examiner

MODALITY WITH MULTICOMPUTER SYSTEM AND POWERING SEQUENCE THEREFOR

CROSS REFERENCE TO RELATED APPLICATIONS

This application claims priority from Provisional Application No. 61/775,358 filed Mar. 8, 2013, the disclosure of which is hereby incorporated by reference herein in its entirety.

FIELD

The disclosure of this application generally relates to computer architecture of multicomputer systems, and in particular it relates to an imaging modality including plural computers and a power-sequence control circuit for controlling activation and deactivation of power supply to the plural computers. An imaging modality including plural computers and a power-sequence control circuit, as disclosed herein, is believed to be applicable to mobile or field deployable medical imaging.

BACKGROUND

Health information technology (health IT) makes it possible to efficiently manage patient care through secure use and sharing of electronic health records (EHRs). EHRs include electronic medical records (EMRs) and other critical data created and regularly consulted and updated by healthcare organizations and their staff. An electronic medical record (EMR) typically includes all of a patient's medical history from a healthcare provider. EMR records are used by healthcare providers, such as hospitals, clinics, medical specialists, and the like to identify patients, track patients' healthcare overtime, check or update on patients' health parameters, monitor and improve overall quality of care. Therefore it is generally necessary to refer to a patient's EMR every time a patient seeks care from a healthcare provider. To that end, healthcare organizations are seeking to implement an EMR infrastructure that is accessible from multiple points of care. The healthcare industry has developed dedicated EMR software applications and dedicated communication protocols which allow a convenient flow of medical data.

Two important elements of the healthcare infrastructure for the flow medial data are PACS (picture archiving and communication system) and DICOM (Digital Imaging and Communications in Medicine). DICOM is the healthcare industry standard for formatting, transferring, storing and viewing EMRs. Based on the Open System Interconnection (OSI) model of the International Standards Organization (ISO), DICOM enables digital communication between diagnostic and therapeutic equipment and systems from various manufacturers. Specifically, DICOM enables the integration of scanners, servers, workstations, printers, and network hardware from multiple manufacturers into a healthcare facility's PACS.

A PACS system consists namely of: (i) an imaging modality; (ii) a secured network (typically TCP/IP network, e.g., Ethernet®) for transmission of patient image data and information related thereto; (iii) workstations for interpreting and reviewing the images, (iv) archiving databases for the storage and retrieval of images and reports; and (v) workstations for providing access to the databases and making the data available to final users. As used herein, the term "modality" will be given its customary meaning as understood by persons having ordinary skill in the art, and as defined by governmental standards. For example, in medical imaging, the term "modality" typically refers to any of various types of equipment or probes used to acquire images of the body, such as X-ray equipment, ultrasound equipment, optical coherence tomography (OCT) equipment, magnetic resonance devices (MRI scanner), computerized tomography (CT) scanners, positron emission tomography (PET) scanners, Nuclear Medicine systems, and the like. Imaging modalities generate large amounts of medical imaging information, such as images, videos, reports, waveforms and audio. Typically this information is spread throughout a healthcare enterprise and not centrally managed.

Traditional imaging modalities are dedicated systems having specialized hardware for processing the large amounts of data generated by imaging patients with specific imaging sensors or probes. These imaging modalities tend to be delicate and expensive devices that must undergo stringent governmental approval (clearance) before being used for patient care. For this reason, imaging modalities are difficult to upgrade or modify. Further, since imaging modalities have specialized components, which, to maintain governmental clearance, must not be modified, traditional imaging modalities are generally not integrated into, or do not interact freely with, the healthcare IT environment of a given healthcare facility.

However, in large healthcare facilities, such as a hospital where patient care is distributed across various departments often located on multiple floors, a technologist needs to repeatedly travel between different departments and/or floors. Therefore, a conventional use scenario of a traditional imaging modality in the above described infrastructure is not efficient. Specifically, according to conventional technology, for example, X-Ray technologists while imaging a patient with a mobile X-Ray system at an exam room (first location), have the need to access software applications on a separate workstation usually located in a radiology department (second location) remote from the exam room. The following is a typical conventional workflow: first, a technologist selects a patient to be examined from a RIS (Radiology Information System) desktop workstation typically located remote from a place where the patient is to be visited/examined. The technologist leaves the desktop workstation and travels to where the mobile X-Ray system (modality) and/or the place where the patient is located. The technologist now locates the information of the patient to be examined from a Work List that resides on the modality. In particular, when the modality is transportable (mobile modality), the technologist would move the modality to specific locations, such as an ER (emergency room department), imaging department, or even a private home where a patient is located. Therein, the technologist performs the X-Ray exam or any pertinent imaging. If possible, the technologist transfers the study images to PACS. At this point the technologist leaves the mobile X-Ray system and travels back to the RIS desktop workstation at the radiology department. At the Radiology department, the technologist opens the PACS client application (PACS software) and performs a Quality Check (QC) of the images transmitted from the modality. If QC is satisfactory, the technologist will switch to the patient management system in RIS to end the study. If the QC is not satisfactory, the technologist will likely repeat the foregoing process until the study QC is satisfactory. The above workflow represents a very inefficient scenario that drastically limits the technologist's productivity, and encumbers the patient's time and comfort when undergoing treatment.

SUMMARY

In view of the above-noted shortcomings, there is a need for a solution that allows fast and secure access to EMRs, RIS and PACS directly from the imaging modality. Specifically, it would be beneficial to provide an imaging modality operable both on its native hardware and on a standard, commercially available, computing device without making modifications to the original hardware. Providing an enhanced workflow, without modifying the original or native hardware of the imaging modality is considered as a significant advantage because the modality will provide access to third party applications while preserving its original functionality, which typically requires governmental approval (for example, FDA clearance). Specifically, if an imaging modality can be used to perform medical imaging with its original hardware, but at the same time it can be used to interface with external third party applications, such as PACS, RIS and EMR, a user could perform the native imaging operations in the original imaging system and also interact with external third party applications on a standard computing device, such as a generic computer. Advantageously, the user can employ the additional computing device to interact with an independent external application directly from the imaging modality, without interfering with the original system, and without expensive hardware modifications or system updates that could potentially void governmental approvals of the imaging modality.

In accordance with at least one embodiment described herein, the instant disclosure is directed to, among other things, an imaging modality which includes a first computer, a second computer, a computer select circuit connected to a manually operable switch and configured to allow an operator to select whether to operate the first computer or the second computer by manually operating the manually operable switch, a single power supply unit configured to supply operating power to the first computer and the second computer; and a power control circuit connected to the first computer and connected to the second computer. The power control circuit outputs a trigger signal to either activate or deactivate a flow of power supply to the second computer in response to the first computer receiving a turn ON or turn OFF input from the operator.

Other modifications and/or advantages of present invention will become readily apparent to persons skilled in the art from the following detailed description in reference to the drawings.

DETAILED DESCRIPTION

In the following description, reference is made to the accompanying drawings which are illustrations of embodiments in which the teachings disclosed herein may be practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail so as to not lengthen the present disclosure unnecessarily. Some embodiments or diagrams described in this application may be practiced on a computer system that includes, in general, one or more processors or microprocessors for processing information and instructions, random access (volatile) memory (RAM) for storing information and instructions, read-only (non-volatile) memory (ROM) for storing static information and instructions, data storage devices such as a magnetic or optical disk and a hard disk drive (HDD) for storing information and instructions, an optional user output device such as a display device (e.g., an LCD monitor) for displaying information to the computer user, an optional user input device including alphanumeric and function keys (e.g., a keyboard) for communicating information and command selections to the processor, and an optional user input device such as a cursor control device (e.g., a mouse or touchscreen) for communicating user input information and command selections to the processor.

As will be appreciated by persons having ordinary skilled in the art, the present examples or at least parts thereof may be embodied as a system, a method or a non-transitory computer program product. Accordingly, some examples may take the form of an entirely hardware embodiment, or an embodiment combining software and hardware aspects that may all generally be referred herein as a "circuit", "module" or "system". Further, some embodiments may take the form of a computer program product embodied in any non-transitory tangible computer-readable medium having computer-usable program code stored therein. For example, some embodiments described below with reference to flowchart illustrations and/or block diagrams of methods (processes), apparatuses (systems) and computer program products can be implemented by computer program instructions. The computer program instructions may be stored in tangible (non-transitory) computer-readable media that can direct or cause a computer or other programmable data processing apparatus to function in a particular manner, such that the instructions stored in the computer-readable media constitute an article of manufacture including instructions and processes which implement the function/act/step specified in the flowchart and/or block diagram.

Figure 1:
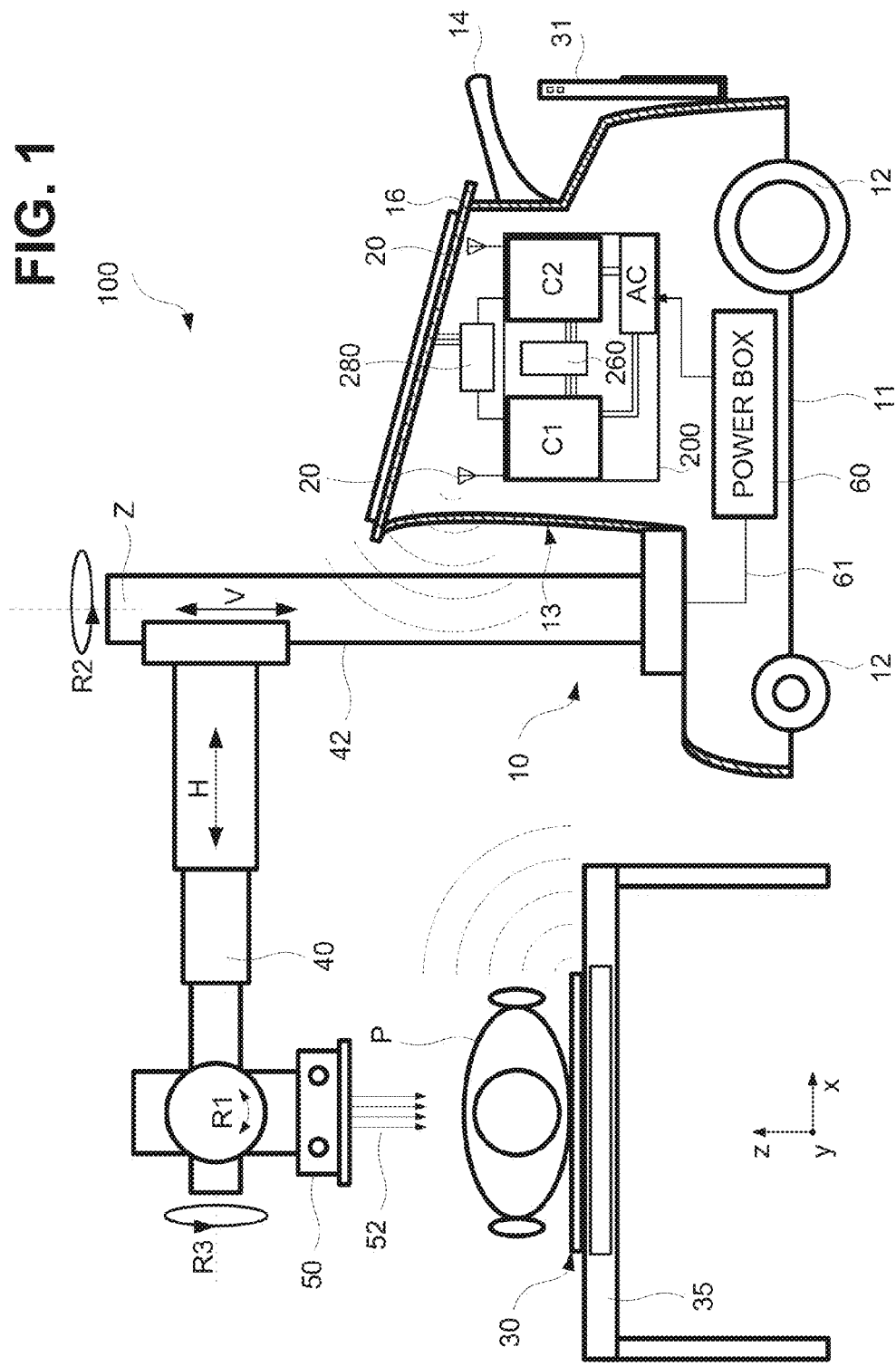
FIG. 1 illustrates an overview of an imaging modality having a multicomputer system.

Referring now to the drawings, where like reference numerals refer to like parts, FIG. 1 an exemplary imaging modality, in accordance with the present disclosure. As illustrated in FIG. 1, an exemplary imaging modality may correspond to a portable radiographic imaging system 100 which includes a radiographic modality 10 (radiographic apparatus) and a digital radiography (DR) sensor 30. An example of the radiographic modality 10 is the RadPRO® 40 kW Digital Mobile X-ray System distributed by Virtual Imaging Inc. of Fort Lauderdale, Fla.; and an example of the DR sensor 30 is the CXDI-70C Wireless Premium Flat Panel Detector available Canon Medical Systems a division of Canon USA Inc. of Melville, N.Y. The radiographic modality 10 includes a console 11 and a radiation source 50 which are physically attached to each other by a vertical column 42 and a horizontal support arm 40. Specifically, the radiation source 50 is attached to the console 11 via the horizontal support arm 40 (movable arm) and the vertical column 42. The horizontal support arm may move vertically (V) along the column 42, may rotate (R2) around an axis Z of the column 42, and may extend telescopically (H).

At the bottom part of console 11 a chassis is mounted on caster wheels 12, so that the radiographic modality 10 can be moved by maneuvering a handle 14. The chassis of the console 11 may be made of metal, such as steel or aluminum. A housing 13 is disposed on the chassis of console 11, so as to enclose therein electronic circuitry and components that serve to control the entire radiographic imaging system 100. The housing 13 also encloses therein electronic circuitry and components that allow the modality to communicate with third party applications, such as EMR, RIS, PACS or the like, directly from the radiographic modality 10. To avoid interference during communication, the housing 13 may be made of a material transparent to radio frequency (RF). On an upper surface of the console 11, within the upper edge of the housing 13, a control panel 16 includes, for example, a liquid crystal display (LCD) with a touchscreen keyboard, a pointing device, push buttons, switches and other like devices to enable a user to interact with the modality.

Enclosed within the housing 13 of the console 11 are included, among other components, a power box 60, and a first computer C1 and a second computer C2 arranged on a single computer chassis 200. Within the computer chassis 200 there are included a computer power supply 15, a computer select circuit 280 and a power control circuit 260. Each of the first computer C1 and the second computer C2 are equipped with one or more wireless antennas 20. The power box 60 may include, for example, a rechargeable battery and control circuitry to supply power for the entire operation of the radiographic modality 10. The power box 60 may be connected to a non-illustrated external power supply or to an existing electric power grid via non-shown cabling, in a known manner. To supply power to the electronics housed within console 11, the power box 60 may be connected by known cabling or circuitry. As illustrated in FIG. 1, the power box 60 is connected to an AC power supply interface of the chassis 200.

The power box 60 also provides operating power to the radiation source 50, the control panel 16 and any other devices necessary for performing imaging operations and communication with third party remote devices directly from the radiographic modality 10. To supply power to the radiation source 50, the power box 60 is connected thereto via cabling 61 which extends along the interior or exterior of the vertical column 42 and the support arm 40. On the exterior of housing 13, console 11 is provided with a compartment for storing the DR sensor 30, or for carrying an additional wireless or wired DR sensor 31.

In operation, the radiographic modality 10 is configured to communicate with the DR sensor 30 via a wireless or wired communication link. In this manner, a user can operate the radiographing modality to perform radiographic imaging of a patient P disposed on a bed or table 35. To appropriately position the radiographic modality 10 with respect to the patient P, the modality 10 can be moved on its caster wheels 12, and the radiation source 50 may be moved in linear directions along x, y and z planes, and/or in circular directions R1, R2 and R3. Communication between radiographic modality 10 and the DR sensor 30 may be implemented by wireless or wired communication links in a known manner. During operation, the radiation source 50 generates radiation 52 by using high voltage power supplied from the power box 60 through cabling 61. An example of the radiation source 50 is an x-ray tube, and an example of the radiation emitted by the radiation source is x-ray radiation. Radiographic images resulting from an examination of patient P may be used for display in the LCD panel of control panel 16, for storage within the imaging modality itself, or for transmission to third party applications.

Figure 2A:
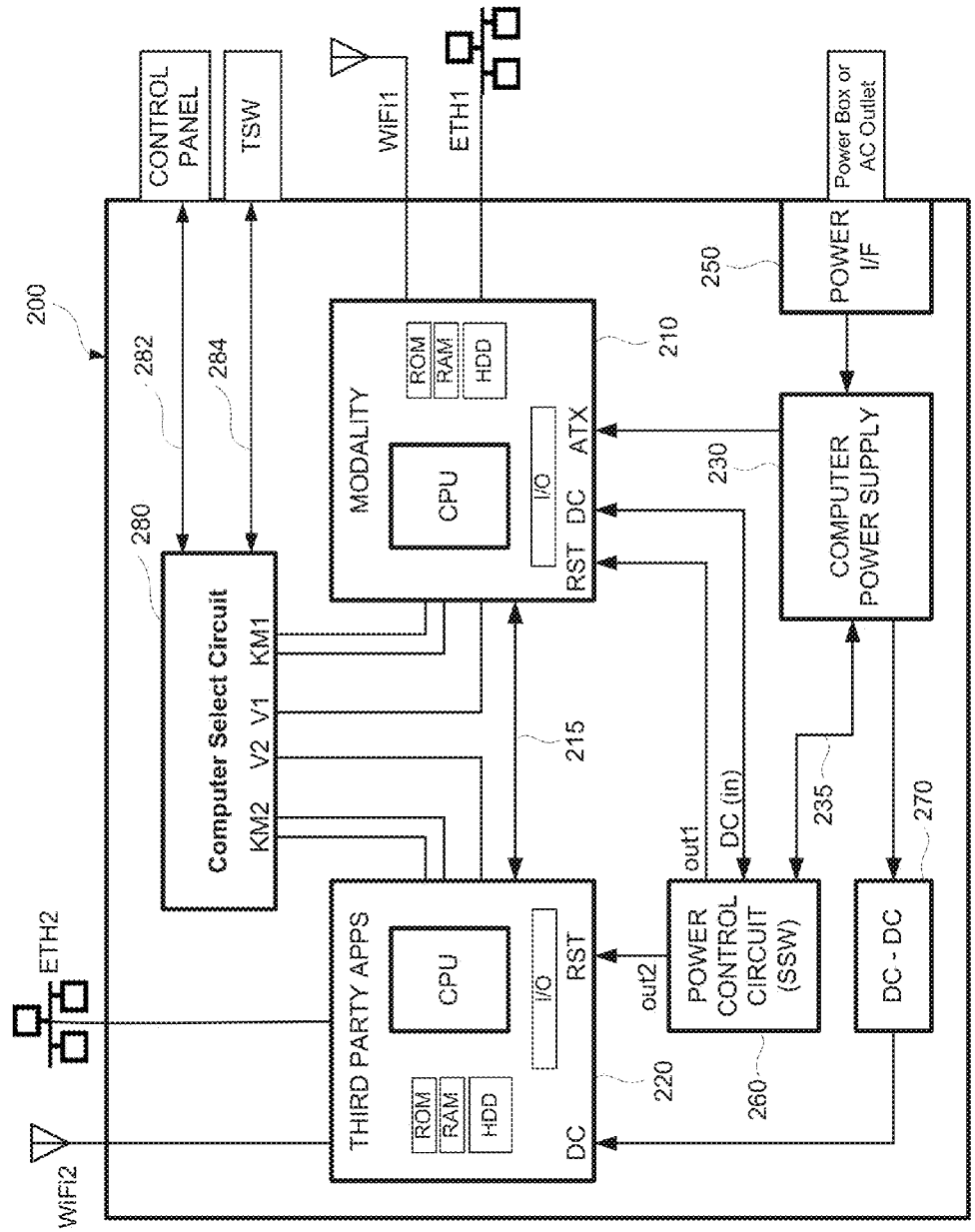
FIG. 2A illustrates a diagram of functional blocks corresponding to a hardware structure of a multicomputer system included in an imaging modality.

FIG. 2A illustrates a functional block diagram of the manner in which the first computer C1 and the second computer C2 are mounted within the console 11 (shown in FIG. 1). As it is known to persons of oridinary skill in the art, computers are an integral part of modern imaging modalities. Computers are used in different imaging modalities to acquire, process, and even post process imaging data. Key hardware components in a modality's computer are the motherboard, the central processing unit (CPU), the chipset, random access memory (RAM), read only memory (ROM), storage drives and input/output ports. These components are interconnected by electrical pathways called "buses".

As illustrated in FIG. 2A, a first computer motherboard 210 (first computer 210) and a second computer motherboard 220 (second computer 220) are mounted on a single computer-chassis 200 (chassis 200). The first computer 210 is equipped with at least one wireless communication link (WiFi1) and at least one wired communication link (ETH1). Similarly, the second computer 220 is equipped with at least one wireless communication link (WiFi2) and at least one wired communication link (ETH2). Each of the first computer 210 and the second computer 220 are implemented by one or more microprocessors, and each computer is sufficiently interconnected to known electronic components to enable each computer to independently operate as desired. The known components include, but are not limited to, a CPU to execute given software programs, a ROM module to store programs, a RAM module into which data used by the CPU to perform calculations are temporarily stored, and an I/O (input/output) port for, among other operations, receiving various signals from either the computer select circuit 280 or the power control circuit 260.

A computer power supply 230 provides operating power to the first computer 210, the second computer 220, and other electronic components arranged within the computer chassis 200. The power supply 230 receives AC electric power from the power box 60 (see FIG. 1) via a power interface 250 (POWER I/F). Therefore, the power interface 250 is connected to a non-illustrated DC to AC converter of the power box 60. However, in addition to (or instead of)

being connected to the power box 60, the power interface 250 may be connected to an external AC power supply source, e.g., to an electric outlet of the power grid existing on the premises on which the imaging modality is to operate. Accordingly, the power supply 230 preferably includes a transformer that transforms AC power to DC voltage sufficient to operate the first computer 210, the second computer 220, and all other equipment within the computer chassis 200. To supply power to the first computer 210 and to second computer 220, a first lead wire of the power supply 230 is connected to an ATX connector of the first computer 210 and a second lead wire is connected to a DC terminal of the second computer 220 via a power converter (DC to DC converter) 270. The power supply 230 is also connected to the power control circuit 260 via a connection lead wire which includes a stand-by line 235.

The power control circuit 260 receives power supply from the power supply 230 via the stand-by line 235, and it is connected to the first computer 210 via an out1 connection, and to the second computer 220 via an out2 connection. The power control circuit 260 serves to control a powering sequence for turning ON and for turning OFF both computers in a manner that ensures appropriate operation of the radiographic modality 10 to simultaneously run imaging operations and third party applications. To that end, the power control circuit 260 actively communicates with the power supply 230 via the connection lead wire which includes a stand-by line 235, with the first computer 210 via the out1 connection, and with the second computer 220 via the out2 connection. More specifically, powering two independent computers from a single power supply requires proper shutdown and start-up control. In accordance with embodiments of the present application, proper shutdown and start-up control is accomplished by the power control circuit 260 which functions as a "smart switch" connected to the frontend of both motherboards. It should be understood that the "connections" between the power control circuit 260, the power supply, and the motherboards of the first and second computers (shown in the drawing of FIG. 2A) are exemplary of generalized logical functionality provided by the power control circuit 260, and therefore these "connections" are not intended to limit or restrict the structural implementation of the power control circuit 260 and interconnections thereof.

Figure 2B:
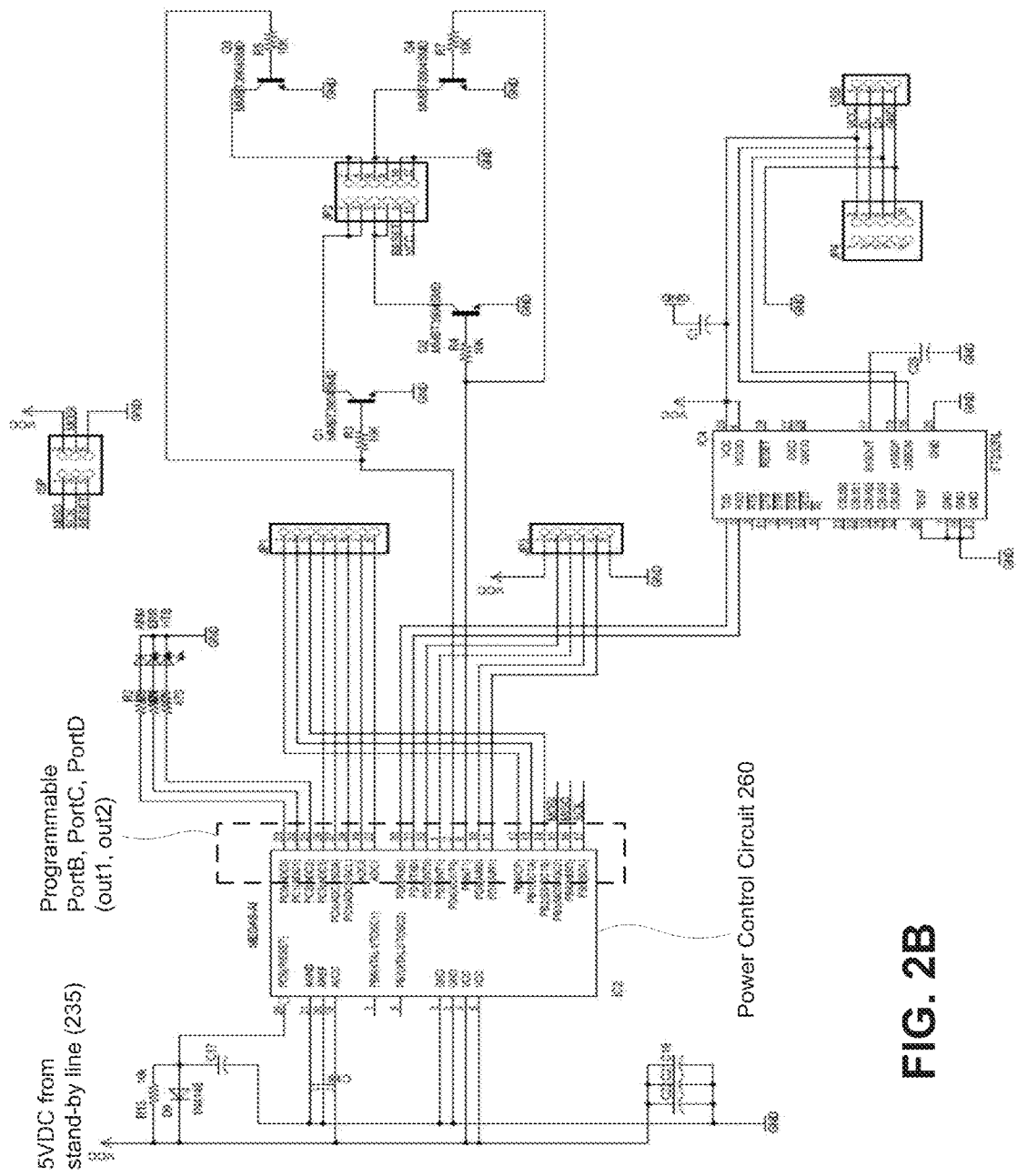
FIG. 2B illustrates an exemplary implementation of a power control circuit configured to control flow of power supply to the multicomputer system based on input from an operator.

The actual electronic structure may be implemented using one or more hardware components and actual connections thereof will vary, as long as such components are configured to (made to) implement and achieve the functionality described herein. Notably, it is advantageous that the power control circuit 260 will directly interface with the modality's power supply, e.g., via an ON/OFF circuit, and with the motherboards of the first and second computers. An exemplary circuit of an actual hardware implementation is shown in FIG. 2B. In FIG. 2B, the power control circuit 260 has been implemented using an 8-bit programmable microcontroller MEGA8-AI from Atmel Corporation of San Jose, Calif. The MEGA8 circuit is a low-power CMOS 8-bit microcontroller based on RISC (reduced instruction set computer) architecture with 8K bytes in-system programmable memory. The timing diagrams and process flowcharts have been programmed into the microcontroller MEGA8. To achieve the functionality of the power control circuit 260, the VCC terminal shown in FIG. 2B, corresponds to the stand-by line signal 235 shown in FIG. 2A. In addition, the connection out1 connected to the first computer 210, and the connection out2 connected to the second computer 220 (shown in FIG. 2A), may be implemented by programming either or each of port B, port C or port D of the microcontroller MEGA8 with respective output and timing signals to implement the timing control and signal flow processes shown in FIGS. 4A to 6B, so that power supply to each motherboard of the first and second computers is operatively controlled by the microcontroller MEGA8. Some of the features already provided in known microcontrollers, such as the MEGA8, are timers and counters and programmable serial and/or parallel outputs. These known features of the microcontroller can be used to implement programmed timing, delays and signal outputs in accordance with the description of FIGS. 4A to 6B.

Specifically, while each motherboard/computer is an independent system, care is taken to provide orderly startup and shutdown in an orderly (or prioritized) manner. To that end, the power control circuit 260 is continuously powered by a 5 VDC stand-by line 235 from the computer power supply 230 provided within the computer chassis 200. This allows the power control circuit 260 to be active even when the state of the imaging modality is OFF or in stand-by mode. In this manner, the imaging modality is configured to, at any time, perform a synchronized powering sequence to ensure that the first computer 210 and the second computer 220 will be turned ON and/or turned OFF in the safest manner possible without jeopardizing operations. The powering sequence of the first computer 210 and the second computer 220 is explained below in detail with reference to FIGS. 4A to 6B.

The power control circuit 260 may be implemented in a number of configurations, as long as the powering sequence allows for selective prioritization, as disclosed herein. Existing patent and non-patent literature documents disclose examples in which power control circuitry is used for controlling time delays of power supply to microprocessor-based systems. However, those examples do not address the unique challenges presented in a situation of a mobile imaging modality. For example, U.S. Pat. No. 6,661,123 (patent '123) discloses a power control circuit with power-off time delay control for a microprocessor-based system. According to patent '123, the time delay control circuit is capable of controlling a turn-on and a delayed turn-off of a switch unit depending on the status of a DC operating voltage. When a manually operable switch is turned on, the AC power supply is supplied to the microprocessor-based system in a normal condition. When the manually operable switch is turned off, the AC power supply is still maintained to the microprocessor-based system for a predetermined delay time. U.S. Pat. No. 8,281,167 (patent '167) discloses an electronic control apparatus for controlling plural microcomputers mounted in a vehicle. According to patent '167, a first power supply unit supplies, via a first supply line, power supply voltage to a main microcomputer for activation, and a second power supply unit supplies, via a second supply line different from the first supply line, power supply voltage to a sub-microcomputer for activation when the sub-microcomputer receives the power control signal. The main microcomputer determines whether or not the sub-microcomputer should be made to operate and performs a switchover between output and non-output of the power control signal to the second power supply unit based on the determined results, whereby the power supply to the sub-microcomputer is controlled.

As noted in the above conventional examples, in patent '123, a delay is provided to a single microprosessor, and in patent '167 two microcomputers are controlled to be supplied power from plural power supplies. However, powering two independent computers from a single power supply requires proper start-up and power-down control. In the present application, sequenced start-up and power-down control is accomplished by the power control circuit 260 which functions as a "smart switch" on the frontend of both motherboards. While each motherboard/computer is an independent system, as described above, care is taken to provide orderly and prioritized startup and shutdown. As mentioned above, the power control circuit 260 is continuously powered from the 5 VDC stand-by line 235 connected to the power supply 230 provided within the computer chassis 200.

The "smart switch" functionality of the power control circuit 260 includes, but is not limited to, the following premise. In an imaging modality, in particular a mobile modality, a rechargeable battery is typically used as the power supply for the entire system. In that case, power supply must be managed appropriately to optimize usage of the power supply, while ensuring safe operations of the modality. For example, to ensure that the imaging modality is primarily used for its intended purpose of imaging, it is important that the computer controlling the imaging modality is first put into operative state. That is, it is important that the computer controlling the imaging modality is first turned ON. This ensures, for example, that the imaging modality is ready to perform imaging operations on a patient. However, at the same time, it advantageous to optimize the comfort of the patient, as well as the productivity of the imaging technician (operator). To that end, the present application proposes including a computer (second) within the imaging modality for accessing third party applications directly from the imaging modality. Therefore, in the present application, the "smart switch" functionality of the power control circuit 260 ensures that immediately after the computer (first computer) which controls the imaging modality is powered ON, the computer (second computer) which controls the third party applications is also powered ON.

Moreover, once the two computers of the imaging modality are operative, and after operations thereof are completed, it is important to ensure that the imaging modality is powered down after it is safe to do so. Specifically, in the present application, care is taken to avoid accidental or unintended powering down of the imaging modality. To that end, the "smart switch" functionality of the power control circuit 260 ensures that the computer (first computer) which controls the imaging modality is powered OFF after the computer (second computer) which controls the third party applications is also powered OFF. This is considered advantageous in the sense that any accidental or unintended power-down inputs will not immediately stop the imaging modality. Instead, as fully described below, when a power-down input is received by the imaging modality, the power control circuit 260 implements an orderly shutdown sequence, which allows the imaging modality to securely and safely stop imaging operations prior to stopping the flow of power supply.

A computer select circuit 280 serves to provide a switchable interface to an operator of the radiographic modality 10, so that the operator can selectably switch operations between the first computer 210 and the second computer 220. Exemplary operations, in which the first computer 210 and the second computer 220 are used independently while operating simultaneously, are explained below with reference to FIG. 7.

The computer select circuit 280 may be implemented in any number of configurations. There are numerous examples of patent and non-patent literature documents that disclose examples in which multiple computers (or multiple computer motherboards) can share the resources of single workstation by using a computer select circuit. For example, U.S. Pat. No. 5,680,536 discloses a dual mother board computer system that shares a single power supply and peripheral components thereof, such as keyboard, mouse and video output. Patent application publication US 2009/0265412 discloses a plural computer system for operating a plurality of computers contained within an enclosure. According to US 2009/0265412 each computer includes a processor, memory, information storage, an operating system, a network interface, a user input/output (I/O) interface. The computers are powered by a single power supply and are interconnected through a KVM switch to enable each computer to independently operate as desired. Therefore, the computer select circuit 280 can be implemented in a manner currently known or in a manner to be developed in the future. As long as the computer select circuit is operably to allow a user of the imaging modality to select alternately and repeatedly one of the first and second computers, the implementation of the computer select circuit is not limited to a particular structure.

As illustrated in FIG. 2A, the computer select circuit 280 includes a first keyboard and mouse terminal (KM1), a first video terminal V1, a second keyboard and mouse terminal (KM2) and a second video terminal V2. The computer select circuit 280 also includes other connections connected to a lead 282 and a lead 284. The lead 282 connects the computer select circuit 280 to the control panel 16, and the lead 284 connects the computer select circuit 280 to a toggle switch TSW. The first keyboard and mouse terminal (KM1) and first video terminal V1 of the computer select circuit 280 are connected to respective keyboard and mouse, and video terminals of the first computer 210. Similarly, the second keyboard and mouse terminal (KM2) and second video terminal V2 of the computer select circuit 280 are connected to respective keyboard and mouse, and video terminals of the second computer 220. In addition, the first computer 210 and the second computer 220 are directly connected to each other via a communication link 215. An example of the communication link 215 is a serial communication cable connected directly to a serial communication port (COM) of each computer.

In one exemplary embodiment, the computer select circuit 280 may be implemented by a known structure of a KVM switch. In that case, the keyboard and mouse terminal (KM1) can be connected to the keyboard and mouse terminals of first computer 210 via universal serial bus (USB) terminals, and the first video signal V1 may be connected to a corresponding video terminal of the first computer 210 in a known manner. Similar connections would be available for connecting to the second computer 220. The toggle switch TSW provides a simplified and easy interface to an operator to swiftly and seamlessly switch between the first and second computers residing within the console of the imaging modality. The output terminal connected to the lead 282 represents a hardware connection from the first and second computers to the control panel 16 (see FIG. 1). A first purpose of computer select circuit 280 is to transmit video signals from either the first computer 210 or the second computer 220 to the LCD display on the control panel 16. In addition, the computer select circuit 280 also serves to transmit user-input signals entered via the control panel 16 into the selected computer. For example, depending on the selection made by an operator via the toggle switch TSW, the operator can use a touchscreen display (in control panel 16) to interact with either the first computer 210 or the second computer 220 to respectively perform imaging operations using the imaging modality or to interact with third party applications, such as an EMR system to provide the results of the imaging operations.

Figure 3A:
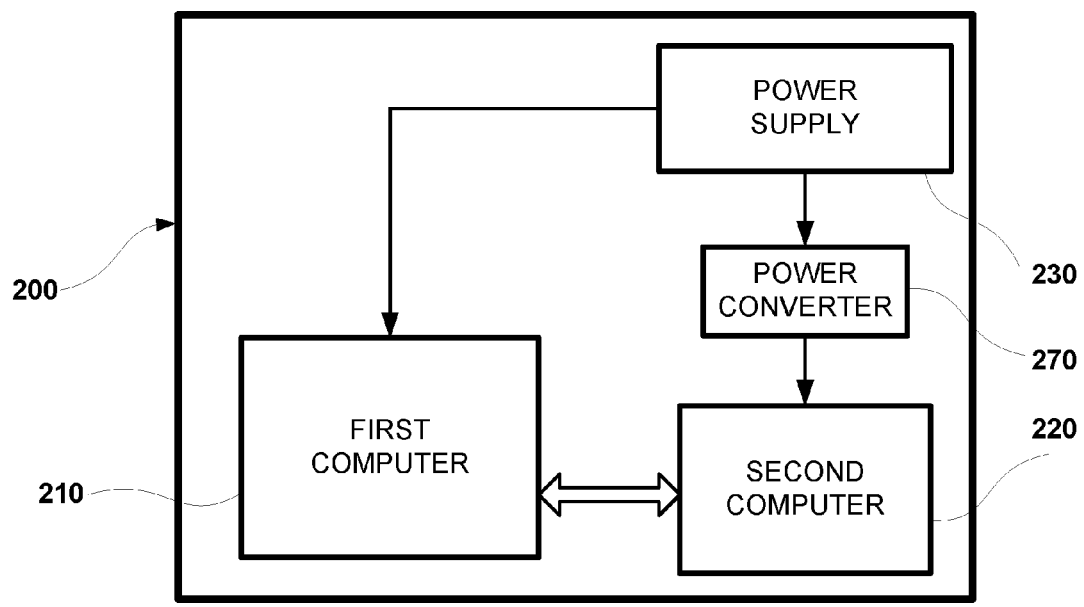
FIG. 3A is a photograph that illustrates an exemplary implementation of a multicomputer system on a single chassis.

FIG. 3A illustrates an exemplary implementation of a single computer chassis 200 (mentioned in FIG. 2A) configured to accommodate therein a first computer 210, a second computer 220, a single power supply 230, a power converter circuit 270, and other electronic components necessary to enable each computer to operate as described herein. Specifically, although not visible in the depiction of FIG. 3A, the power control circuit 260 may also be disposed within the chassis 200, so that the power control circuit 260 can be connected to the 5 VDC stand-by line 235 of the power supply 230 (see FIG. 2A).

Figure 3B:
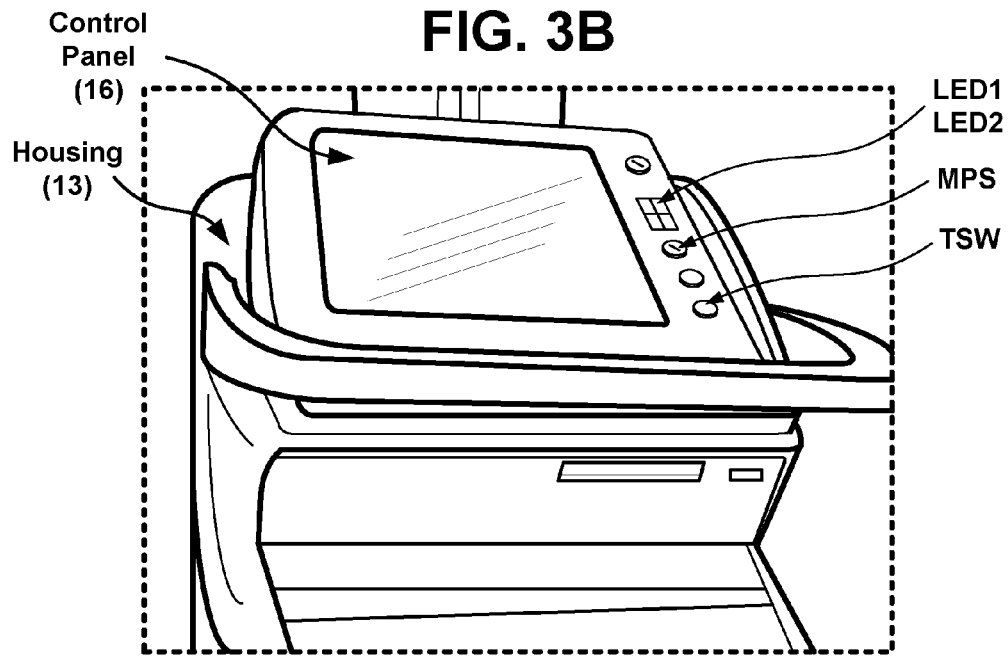
FIG. 3B is a photograph that illustrates an exemplary implementation of a control panel (user interface) of the imaging modality; the control panel allows an operator of the imaging modality to control and operate the multicomputer system.

FIG. 3B illustrates an exemplary implementation of the control panel 16 (user interface) including a liquid crystal display (LCD) with a touchscreen keyboard (not shown), push buttons to control operations thereof, switches and the like. The control panel 16 is provided assembled (integrated) within the upper edge of the housing 13. The control panel 16 may be implemented by a panel already existing in an imaging modality or it may use a newly designed control panel. Notably, in accordance with an embodiment disclosed herein, a toggle switch TSW (also shown in FIG. 2A) is provided as part of the user interface, so that an operator can, by simply operating the toggle switch TSW, may seamlessly switch between the first computer 210 and the second computer 220. On the control panel 16, additionally illustrated are a main power switch MPS (the modality's main power switch), and light emitting diodes (LED1 and LED2). In accordance with this application, LED1 and LED2 are operatively connected to the first computer 210 and the second computer 220, respectively. Each of LED1 and LED2 serves as a power-ON indicator or display to inform the modality's operator of the active (ON) or non-active (OFF) state of each of the first computer 210 and second computer 220, respectively. To that end, LED1 and LED2 may in addition, or instead, be operatively connected to outputs of the power control circuit 260.

To keep with an objective of minimal modification to the original hardware of the imaging modality, it is preferable that the single chassis 200 would match a known or standardized computer chassis that fits within the space provided inside the imaging modality. The computer chassis is not restricted to specific models or dimensions, as long as such computer chassis can accommodate at least the two computer motherboards (motherboard of computer 1 and motherboard of computer2), and the additional circuitry necessary to enable the two computers to operate independently for their intended purpose. For example, in the case where a conventional single-motherboard imaging modality is being updated to a dual-motherboard imaging modality, a first motherboard (the first computer 210) would correspond to the computer already existing in the modality; and a second motherboard (the second computer 220) can be a small footprint computer provided to execute "site specific" third party applications.

As mentioned above, an example of a radiographic modality 10 (mobile imaging modality) is the RadPRO® 40 kW Digital Mobile X-ray system. In that case, the first computer 210 would consist of an ITOX motherboard for Canon CXDI control which is typically provided within the RadPRO® 40 kW Digital Mobile X-ray system; and the second computer 220 may consist of, for example, an Intel NUC style motherboard. In this example, when implemented as disclosed herein, the Intel NUC style motherboard would run (operate) parallel to the ITOX motherboard, but independently from it. Specifically, the ITOX motherboard will control the entire operation of RadPRO® 40 kW Digital Mobile X-ray system, and the Intel NUC style motherboard would independently operate to control access to third party applications, such as Cerner, Epic, Impax, etc. Further, in this example, the toggle switch TSW mounted on the control panel would allow an operator (imaging technologist) to seamlessly switch between the Canon CXDI control computer and the Intel NUC style computer to selectively and/or simultaneously perform imaging operations and access third party applications without leaving the site where the imaging modality is being used.

From the foregoing description, it should be appreciated that a conventional modality typically lacking access to third party applications such as, PACS or EMR, can be modified and updated to improve its productivity without making significant changes to the original government-approved hardware. Specifically, in a conventional imaging modality, the existing computer motherboard would be assigned the position or task of a "main computer" (first computer 210 in the drawings). And an additional off-the-shelf small footprint computer can be accommodated within (or attached to) the chassis of the existing computer with minimal hardware modifications. That is, in order to update a conventional single-computer modality to a multicomputer modality, the power control circuit 260 (also refereed herein as the smart switch SSW) and the computer-select switch can be added with minimal hardware configuration, as described above. Therefore, the conventional imaging modality and its existing computer motherboard would remain essentially unchanged, but the functionality of the modality would become significantly improved by allowing the operator to access "on site" third party applications without leaving the imaging modality or the patient.

<Powering Up (Turn ON) Sequence>

Figure 4A:
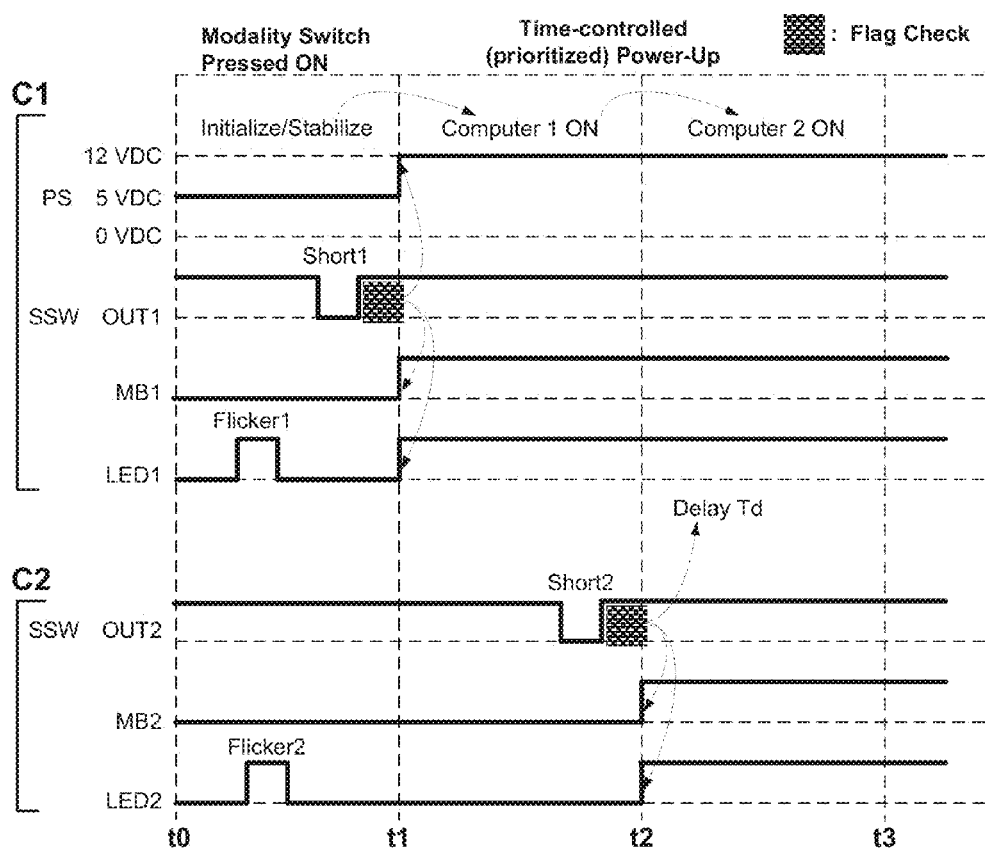
FIG. 4A is a timing diagram and FIG. 4B is flowchart to graphically illustrate an exemplary process of a powering-up sequence of the multicomputer system.
Figure 4B:
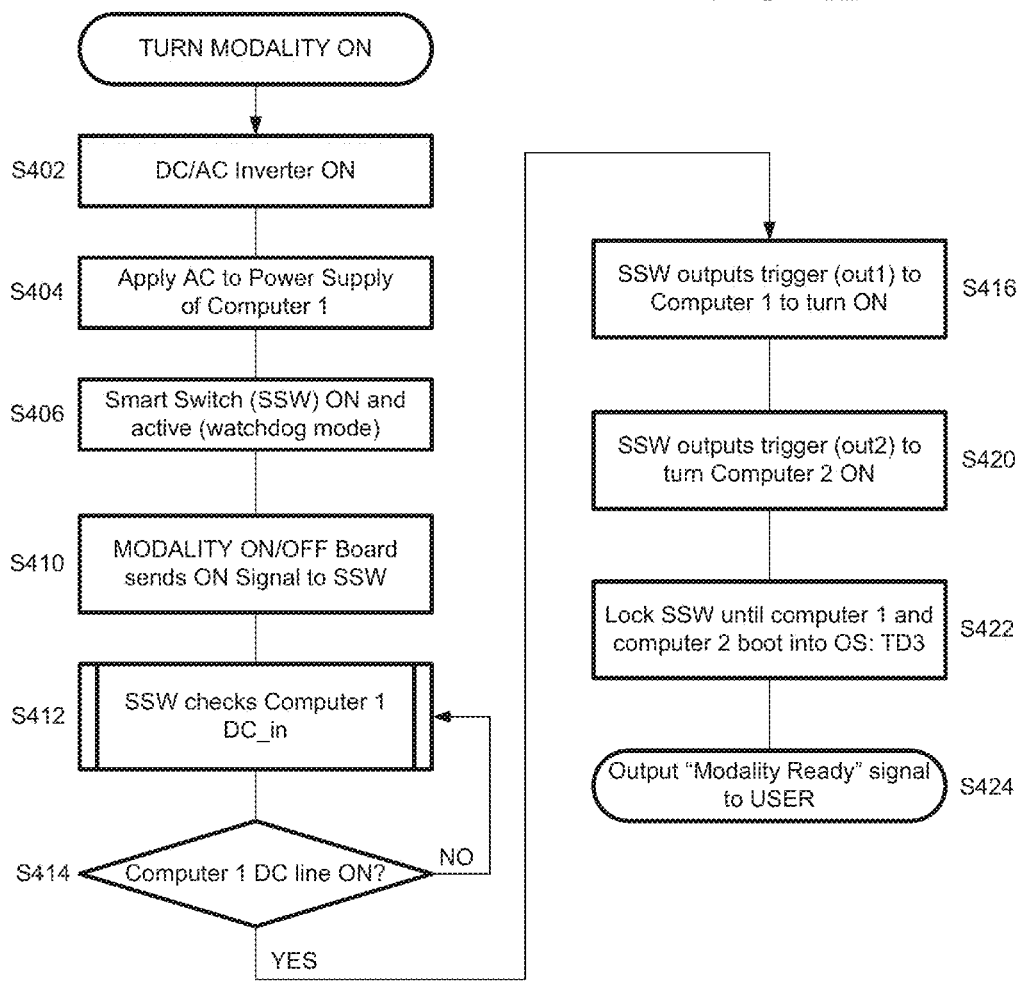

FIG. 4A is a timing diagram and FIG. 4B is flow chart to graphically illustrate an exemplary process of a powering-up sequence of an imaging modality with a multicomputer system. In FIG. 4A, C1 represents the first computer 210 or the modality main computer; C2 represents the second computer 220 or the third party or slave computer. PS represents voltage potential levels (power signals) at the ATX connector of the first computer 210. OUT1 represents a voltage potential level (output signal) at a first terminal out1 of the power control circuit 260 (smart switch SSW). MB1 represents an operational state of the motherboard in the first computer 210; and LED1 represents a signal indicative of an operating or operative state of the first computer. OUT2 represents a voltage potential level (output signal) at a second terminal out2 of the power control circuit 260 (smart switch SSW). MB2 represents an operational state of the motherboard in the second computer 220; and LED2 represents a signal indicative of an operating or operative state of the second computer. LED1 and LED2 also represent the signals of the LEDs shown on the control panel 16 shown in FIG. 3B. Forward arrows from left to right of the figure represent a timed sequence in chronological order in which power supply is provided to first and second computers residing within the modality. Vertical arrows represent signal triggered by an impulse (short) occurring in the illustrated "out" signal.

In FIG. 4A, at an initial time t0, the modality's main power switch (MPS in FIG. 3) is first activated (e.g., momentarily pressed-if pushbutton switch, or key briefly turned and released-if turnkey switch). During the momentary pressing of the modality's main power switch, the first computer C1 and the power control circuit 260 SSW undergo an initialization and stabilization process. Specifically, as described above, the power control circuit 260 is continuously powered by the stand-by 5 VDC line from the power supply 230. Therefore, when the MPS is momentarily pressed, the LED1 and LED2 which are operatively connected to the power control circuit 260 briefly flicker (flicker1 and flicker 2), and the power control circuit 260 generates a first momentary short (short1).

Once a main power switch of the modality is activated, after short1, the power control circuit 260 checks an input flag F1, by sensing a voltage potential in the ATX connector of the first computer 210 (MB1). If the power control circuit 260 senses 0 VDC in the input line of the modality's computer (master computer/motherboard: MB1), power control circuit 260 sends a signal to the power supply 230 to allow the full flow of power supply (the level of PS signal becomes 12 VDC). At this time t1, power control circuit 260 also triggers the master PC to turn ON, and causes the LED1 to turn ON. A few seconds later (2-5 seconds) another momentary short ("short2")) on out2 of the power control circuit 260 is sent to the secondary motherboard (slave computer) to turn it ON. Here too, the power control circuit 260 checks for an input flag F2 by sensing a voltage potential at a DC line in of the second computer motherboard. If the flag F2 is low or negative (F2=0), the power control circuit 260 sends a trigger signal to the power supply switch of the second computer 220. Therefore, at time t2, the power supply signal of MB2 goes high, which means that the second computer is turned ON, and in turn LED2 is turned ON. Thereafter, the power control circuit 260 is locked out until a delay period of approximately 15 to 30 seconds has elapsed to allow adequate time for both computers to boot into their respective operating system (OS). When the power control circuit 260 is locked out the first and second computers are not operative, and therefore, the imaging modality is also effectively lockout to avoid any unintended operation or damage to other elements of the modality. Therefore, at time t3, both computers are fully functional and can operate selectively and or simultaneously. In turn, the modality is also fully functional. Here, it should be noted that a time period necessary for the power control circuit 260 to check a flag and trigger a power ON signal has been indicated as a gray area. The time period represented by the gray area may be very short and may represent a simple logic transition, or it may represent an actual time delay or even a repeated process until the status of the flag has been established.

FIG. 4B illustrates a flow process of a power-up routine for a chronological operation of powering up the first computer 210 and the second computer 220. The flow process of FIG. 4B represents a process of tuning the imaging modality ON and starting-up the computer that runs the imaging modality (main computer) in a prioritized manner with respect to a sub-computer (slave computer) that runs third party applications. To start the flow process, the modality is assumed to have been previously powered OFF, but at time t0 of FIG. 4A it is powered ON by, for example, operating on a main power switch to enable connection between the power supply (power box 60) of the imaging modality and the modality electronics. Therefore, at step S402, once the main power switch is pressed ON, a DC/AC inverter (not shown) of the modality power box 60 becomes active. Once the power box 60 of the modality is ON, at step S404, alternate current (AC) is applied to a terminal of the first computer 210 (the computer that controls the modality). Next, at step S406, the power control circuit 260 (smart switch SSW) is powered up and activated. In the active state, the power control circuit 260 acts as a "watch dog" and continuously checks an input flag F1 corresponding to an operative status of the first computer 210 and second computer 220. Specifically, at step S410, the modality ON/OFF board (no shown) sends a power ON signal to the power control circuit 260. This "power ON" signal is to activate or power-up the modality's computer (first computer 210). In response to receiving the power ON signal, the power control circuit 260 checks to see (senses) if the modality's computer (first computer) is in an ON or OFF state. To that end, at step S412, the power control circuit 260 detects the flag F1 corresponding to an input sense line (senses the DC_in line) of the modality's computer. For example, as shown in step S414, if the DC_in line of the modality's computer exhibits 0 VDC, it means that the first computer 210 (the modality's computer) is OFF (not active state). If, on the other hand, the DC_in line of the modality's computer is at a voltage potential greater than a threshold level, for example, 5 VDC, the modality's computer is already ON. That is, at step S414, if the modality's computer is OFF, the power control circuit 260 yields a positive result (YES), and the flow process advances to step S416. However, if the modality's computer is already ON, the power control circuit 260 yields a negative result (NO), and the process returns to S412, where power control circuit 260 continuously monitors the DC_in line of the modality's computer as a "watchdog" until power in the DC_in line is sensed.

At step S416, the power control circuit 260 outputs a trigger signal (out1) to the modality's computer (first computer) to turn ON. This is represented in the time diagram of FIG. 4A the arrows pointing up and down at time t1. At step S418, the first computer starts boot-up process. At step S420, at time t2 of FIG. 4A, the power control circuit 260 outputs a second trigger signal (out2) to turn the second computer 220 (slave computer) ON. Once the second computer has been triggered to turn ON, at step S422, the power control circuit 260 is locked-out for a relatively long delay (e.g., 30 seconds or more) to allow adequate time for both computers to boot into their respective operating system (OS). The time delay at step S422 is represented as the period between time t2 and time t3 in FIG. 4A; this period will depend, among other things, on the boot-up speed and processing power of the first and second computers, and may be adjusted as necessary. As long as the power control circuit 260 is configured to ensure that the first and second computer are powered up in this order, and as long as the computers complete the boot-up process, the delay period between t2 and t3 may even be eliminated. That is, as long as the power control circuit 260 can implement a delay sufficient to allow both computers to boot into their operating systems, there is no limitation as to the length of the delay.

At step S424, once both computers are operative, the power control circuit 260 may issue a "Ready" signal to inform the user of the imaging modality that it is safe to operate either one of the two computers, as desired. The "Ready" signal may be provided as, for example, a visual, audible, or haptic output, for example, by displaying a message on the LCD screen of control panel 16, sounding a beeping signal on the control panel 16, or changing the color of LED1 and LED2. A more specific example of a signal indicative that the two computers are ready to be used, may include a log-in prompt displayed on the LCD screen of panel 16.

<Hardware Shutting Down (Turn OFF) Sequence>

Figure 5A:
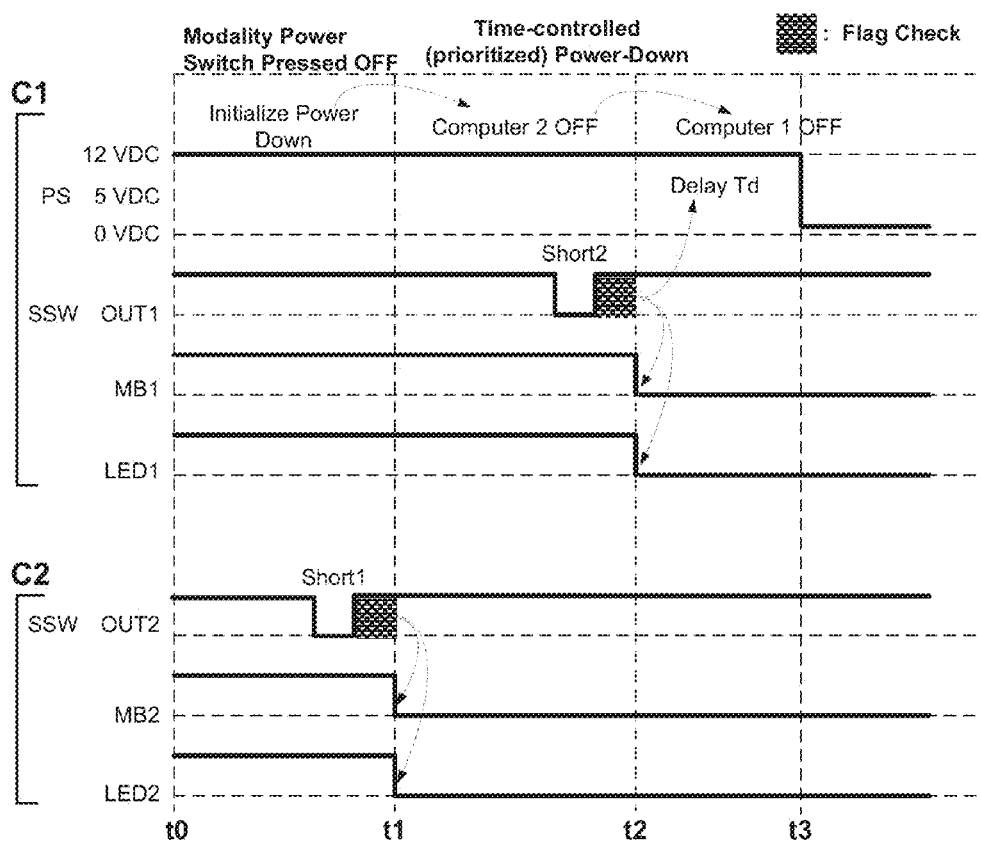
FIG. 5A is a timing diagram and FIG. 5B is flowchart to graphically illustrate an exemplary process of a hardware powering-down sequence of the multicomputer system.
Figure 5B:
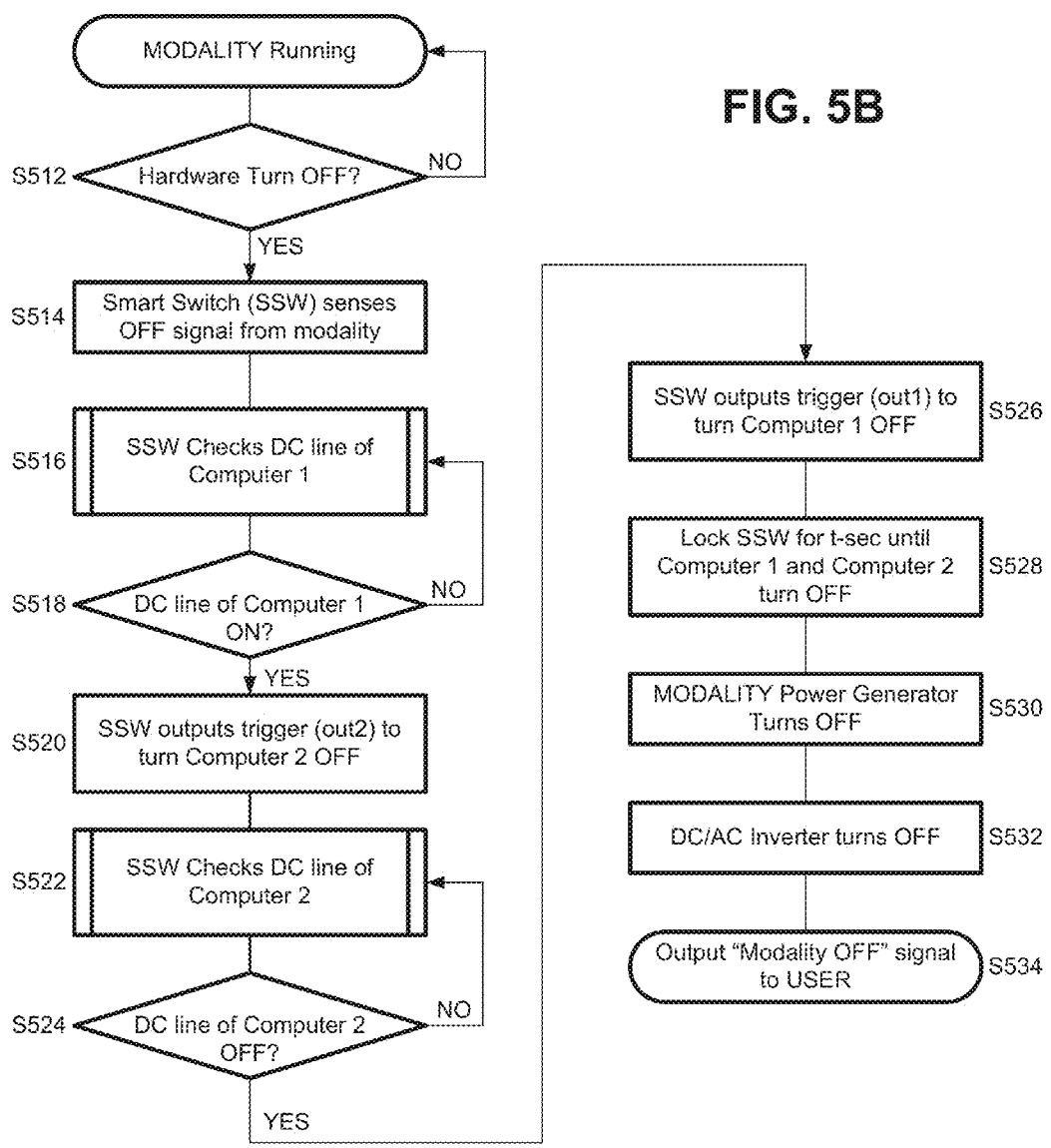

FIG. 5A is a timing diagram and FIG. 5B is flow chart to graphically illustrate an exemplary process of a hardware powering-down sequence of the multicomputer system. In FIG. 5A, signal levels are substantially the same as those described with reference to FIG. 4A. Therefore, repetitious description thereof is omitted. Forward arrows from left to right of the figure represent a timed sequence in chronological order in which power supply cut-off to second and first computers residing within the modality. In FIG. 5A, at an initial time t0, the modality's main power switch (MPS in FIG. 3) is first activated (e.g., momentarily pressed-if pushbutton switch, or key briefly turned and released-if turnkey switch). In this case, the operation is to switch from an active (ON) state to a non-active (OFF) state. Specifically, during the momentary pressing of the modality's main power switch, the second computer C2 and the power control circuit 260 SSW initialize a power down process. Specifically, as described above, since the power control circuit 260 is continuously powered by the stand-by 5 VDC line from the power supply 230, the power control circuit is in a constant "watch dog" state.

That is, once the power ON/OFF switch of the modality is momentarily operated to turn the modality OFF, the power control circuit 260 checks the input flag F1 of the first computer by sensing the 5 VDC line of the first computer 210 (master computer). Since the first computer is in operative (ON) state, a momentary short "short1" causes the power control circuit 260 to now check the flag F2 of the second computer 220, by also sensing the DC input line. After confirming that the second computer is indeed in active (ON) state, the power control circuit 260 outputs a trigger signal to the second computer 220 (slave computer) to shutdown. After the DC voltage in the slave computer goes low (the flag F2 is changed to low: F2=0). Then, another momentary short "short2" causes the power control circuit 260 to again check the flag F1 of the first computer. Since the first computer is still active (ON), the control power circuit 260 outputs a trigger signal to the master computer to shutdown at time t2. Thereafter, the power control circuit 260 is locked out (not sensed) for a period of approximately 12-30 seconds to allow adequate time for both computers to shut down. In this manner, the second and first computers are shutdown in this order in a safe and orderly manner.

FIG. 5B is flow diagram to graphically illustrate the flow process of a hardware powering-down sequence of the imaging modality 10. To start, it is assumed the imaging modality has been in operative state (ON state) and is actively "running" normal imaging operations and third party applications. At this state, represented as t0 in FIG. 5A, the power control circuit 260 acts as a "watchdog" in that at step S512 it continuously monitors whether an OFF input is received. For example, the power control circuit 260 can detect whether the main power switch of the imaging modality 10 has been acted upon to turn the modality OFF. Since a "power OFF" signal would suppress voltage supply to the modality's computer (main computer), once an OFF input signal is detected (YES at S512), the flow advances to step S514. At step S514, the power control circuit 260 receives an OFF signal from the modality's ON/OFF board or switch. At step S516, the power control circuit 260 checks the DC_in line of the first computer 210 (main computer). That is, in response to receiving the power OFF signal, the power control circuit 260 checks to see if the modality's computer is in an ON or OFF state. To that end, at step S518, the power control circuit 260 detects a flag F1 corresponding to an input sense line (senses the DC_in line) of the first computer 210 (modality's computer). If the DC_in line of the modality's computer exhibits a voltage potential equal to or greater than an established threshold (e.g., 5 VDC), it means that the first computer 210 (the modality's computer) is still in ON state (active state) and needs to be shutdown. If, on the other hand, the DC_in line of the modality's computer is at a voltage potential of 0 VDC or close thereto (lower than a threshold level), the modality's computer is already OFF. That is, at step S518, if the modality's computer is ON, the power control circuit 260 yields a positive result (YES), and the flow process advances to step S520.

At step S520, corresponding to time t1 of FIG. 5A, the power control circuit 260 outputs a trigger signal (out2) to turn the second computer 220 OFF. To that end, at step S522 to S524, the power control circuit 260 checks the DC_in line of the second computer 220 until the DC_in line of second computer 220 exhibits a voltage potential of 0 VDC or close thereto (lower than a threshold level). When the DC_in line of the second computer 220 is at 0 VDC or close thereto (YES at S524), the flow proceeds to S526. At step S526, corresponding to time t2 in FIG. 5B, once the second computer (slave computer) is in the process of turning OFF, the power control circuit 260 outputs a trigger signal (out1) to turn the first computer 210 (main computer) OFF. After that, at step S528, the power control circuit 260 is locked-out for a period of time sufficient to allow for both computers to respectively run their OS shutdown routines. This period of time is indicated as "Delay Td" from time t2 to time t3 in FIG. 5A. After the first and second computers have terminated their shutdown routines, at step S530, the power generator of the modality turns OFF; the power supply line PS of the first computer C1 goes low to 0 VDC, as shown after time t3 in FIG. 5A. Specifically, after both motherboards are turned off, a signal is sent to the shared computer power supply to shutdown. When the computer power supply is shutdown a signal is sent to the modality to turn the modality OFF. This, in turn, turns OFF the DC/AC inverter at step S532. An optional acknowledgment or OFF signal can be issued to inform the user of safe shutdown at step S534.

<Software Shutting Down (Turn OFF) Sequence>

Instead of initiating the power-down sequence by acting on the main power switch of the imaging modality, it is also possible to power down the imaging modality directly from the operating system or imaging application running on the modality's computer (main computer). However, as discussed above, when a power-down sequence is performed, care must be taken to ensure the second or slave computer powers down before the first or main computer. More specifically, to ensure safe operation of the two motherboards it will be necessary to enforce a proper power down routine of the master and slave computers. To that end, in one embodiment, a software application compatible with the operating system of master computer can be installed as a plug-in application running on the master computer. In one example implemented by the inventors herein, the software application runs as a Windows® service and implements an event handler (OnShutdown) that captures the Windows message "WM_QUERYENDSESSION" which is triggered by the modality's operator via either (a) Windows shutdown command (e.g. start->shutdown) or (b) imaging system shutdown (e.g. CXDI NE application shutdown). In this case, the start of the power-down routine is controlled by the software application that will continually monitor the operating system (OS) of the master computer for incoming messages in reference to a power-down (turn OFF) command. If a shutdown message is received, a call to the Smart Switch will be made via serial port communication protocol. The software application communicates with the power control circuit 260 by using the .NET SerialPort class via the second computer. Once the shutdown message is received by the power control circuit 260, the power control circuit 260 initiates the shutdown sequence as described below. That is, when a shutdown command is issued by the main computer, the command is forwarded to the slave or second computer via the direct communication link 215 (see FIG. 2A), and power control circuit 260 senses the status of the two computers in a manner similar to the hardware power-down case.

Figure 6A:
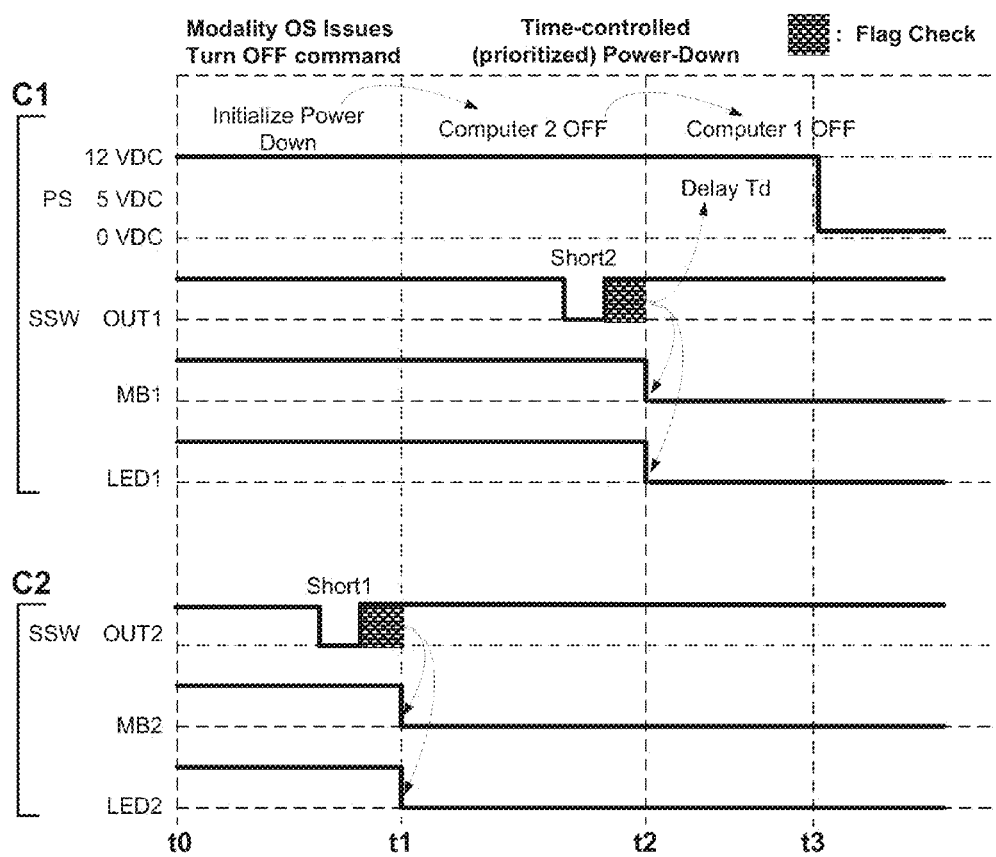
FIG. 6A is a timing diagram and FIG. 6B is flowchart to graphically illustrate an exemplary process of a software powering-down sequence of the multicomputer system.
Figure 6B:
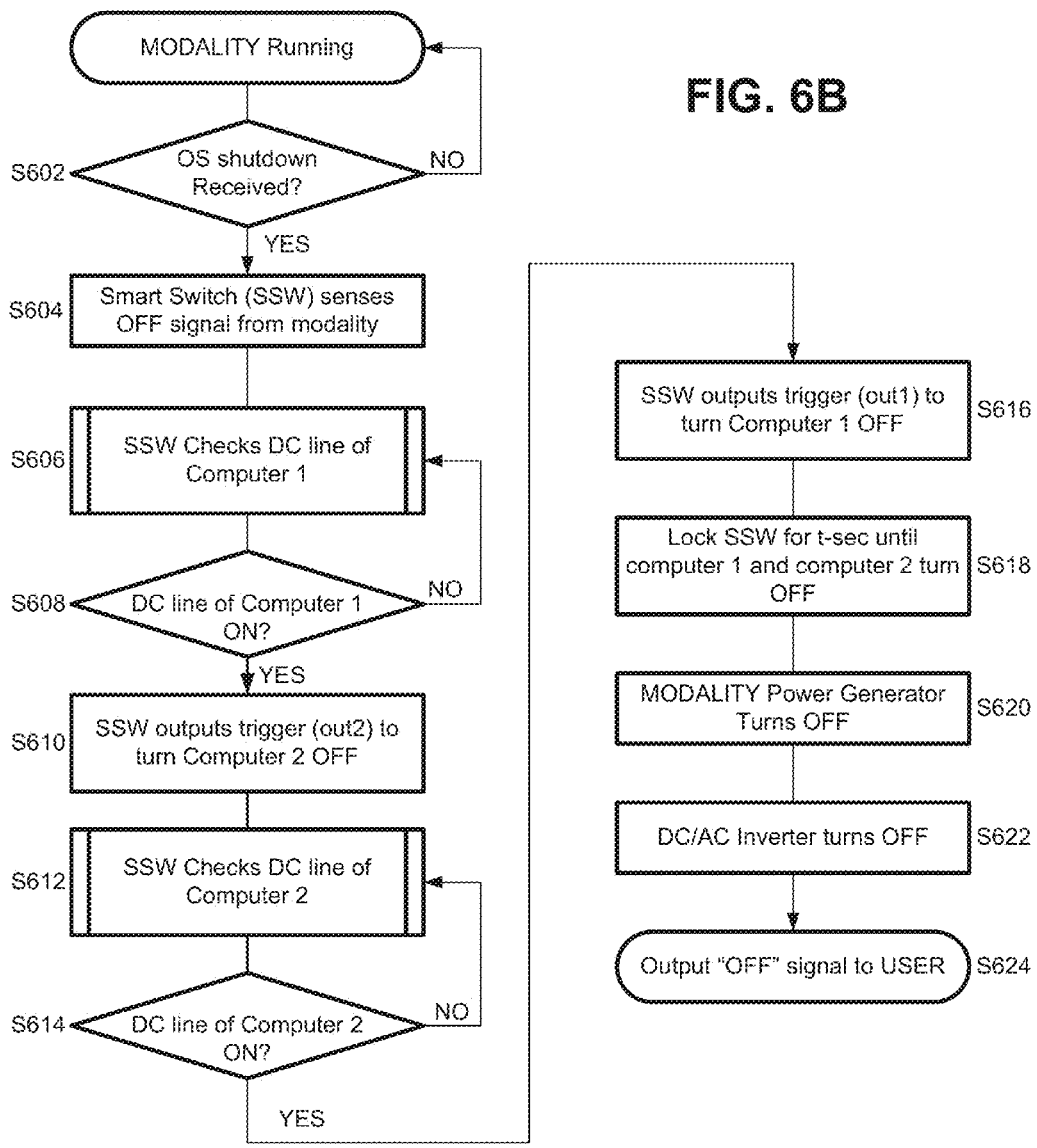

FIG. 6A is a timing diagram and FIG. 6B is flow chart to graphically illustrate an exemplary process of a software-initiated powering-down sequence of the multicomputer system. In FIG. 6A, signal levels are substantially the same as those described with reference to FIG. 4A. Therefore, repetitious description thereof is omitted. In FIG. 6A, at an initial time t0, the modality's main power operating system or imaging application receive a command (Turn OFF command) entered by the modality's operator. In this case, the command is to switch from an active (ON) state to a non-active (OFF) state. The software shutdown detected on the main or first computer activates a signal sent to the second computer via serial port communication. Both computers are now in shutdown mode. The smart switch SSW detects 0 v flags indicating that both motherboards are in a power OFF state. The smart switch SSW now sends a signal to the computer power supply to turn it OFF. The power supply now turns itself OFF.

That is, once the power-down command is received by the first (master) computer, the software application communicates with the power control circuit 260 by using the .NET SerialPort class via the second computer. Once the shutdown message is received by the power control circuit 260, the power control circuit 260 initiates the shutdown sequence. To that end, the power control circuit 260 checks the input flag F1 of the first computer by sensing the 5 VDC line of the first computer 210 (master computer). Since the first computer is still in operative (ON) state, a momentary short "short1" causes the power control circuit 260 to check the flag F2 of the second computer 220, by also sensing the DC input line. After confirming that the second computer is also in active (ON) state, the power control circuit 260 outputs a trigger signal to the second computer 220 (slave computer) to shutdown. After the DC voltage in the slave computer goes low (the flag F2 is changed to low: F2=0). Then, another momentary short "short2" causes the power control circuit 260 to again check the flag F1 of the first computer. Since the first computer continues to be active (ON), the control power circuit 260 outputs a trigger signal to the master computer to shutdown at time t2. Thereafter, the power control circuit 260 is locked out (not sensed) for a period of approximately 12-30 seconds to allow adequate time for both computers to shut down. In this manner, the second and first computers are shutdown in this order in a safe and orderly manner.

FIG. 6B is a flow diagram to graphically illustrate the process of a software powering-down sequence of the multicomputer system. To start, it is assumed the imaging modality has been in operative state (ON state) and is actively "running" normal operations. At this state, represented as time t0 in FIG. 6A, the power control circuit 260 acts as a "watchdog" in that the step S602 is continuously repeated to monitor whether a power-down system call is received from the operating system of the first computer 210 (master computer). Although, it is also possible that a shutdown application could run in the slave computer (second computer 220), and the power-down system call may be issued by the operating system of the slave computer (second computer 220), for safety reasons it is preferable that the power-down system call is started by the first computer 210 (i.e., the computer that controls the imaging modality). In this manner, it can be ensured that the imaging modality ends all imaging operations prior to shutting its computer down.

In any case, once a power OFF input signal (system call) is received at the power control circuit 260 (YES at S602), the flow advances to step S604. At step S604, the power control circuit 260 receives an OFF signal from the operating system of the modality's computer. At step S606, the power control circuit 260 checks the DC_in line of the main computer. That is, in response to receiving the power OFF system call, the power control circuit 260 checks to see if the modality's computer is in an ON or OFF state. To that end, at step S608, the power control circuit 260 detects the flag F1 corresponding to an input sense line (senses the DC_in line) of the modality's computer. If the DC_in line of the modality's computer exhibits a voltage potential equal to or greater than an established threshold value (e.g., 5 VDC), it means that the first computer 210 (the modality's computer) is still in ON state (active state) and needs to be shutdown. If, on the other hand, the DC_in line of the modality's computer is at a voltage potential of 0 VDC or close thereto (lower than a threshold level), the modality's computer is already OFF. Therefore, at step S608, if the modality's computer is ON, the power control circuit 260 yields a positive result (YES), and the flow process advances to step S610.

At step S610, the power control circuit 260 outputs a trigger signal (out2) to turn the second computer 220 OFF; this is represented by the arrows at time t1 in FIG. 6A. To that end, at step S612-614, the power control circuit 260 checks the DC_in line of the second computer 220 until the DC_in line of the second computer 220 exhibits a voltage potential of 0 VDC or close thereto (lower than a threshold level). When the DC_in line of the second computer 220 is at 0 VDC or close thereto (YES at S614), the flow proceeds to S616. At step S616, once the second computer (slave computer) is in the process of turning OFF, the power control circuit 260 outputs a trigger signal (out1) to turn the first computer 210 (main computer) OFF; this is shown by the arrows at t2 in FIG. 6B. After that, at step S618, the power control circuit 260 is locked-out for a period of time sufficient to allow both computers to respectively run their OS shutdown routines. This period of time is shown as "Delay Td" between time t2 and t3 in FIG. 6A. After the first and second computers have terminated their shutdown routines, at step S620, or time t3 in FIG. 6B, the power generator of the modality turns OFF. Therefore, the power supply signal PS goes low to about 0 VDC. This, in turn, turns OFF the DC/AC inverter at step S622. At this time, an optional acknowledgment or OFF signal can be issued to inform the user of the safe powering down sequence at step S624.

<Exemplary Workflow of Use Case Scenario>

Figure 7:
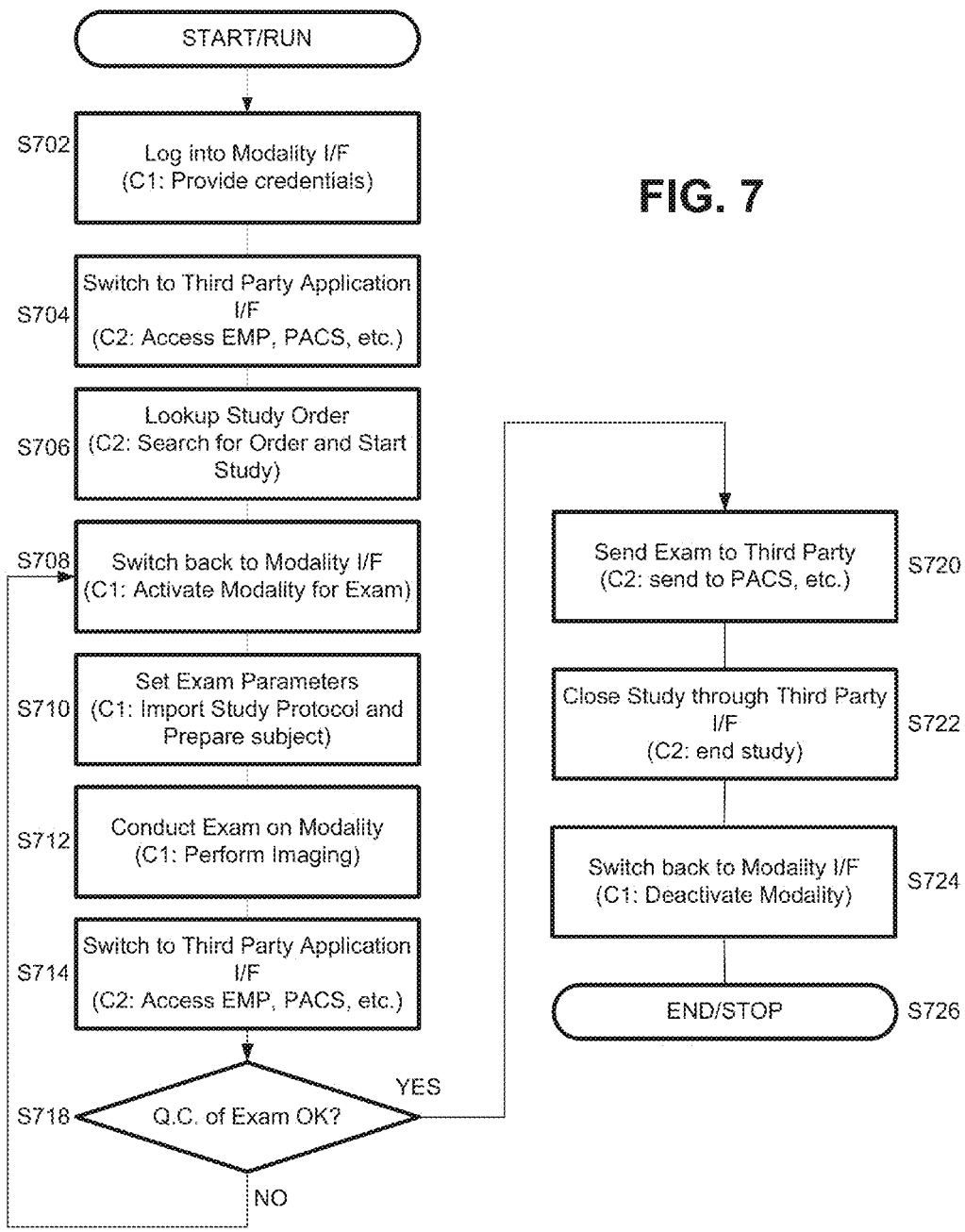
FIG. 7 is a flowchart which illustrates an exemplary workflow process for selectively operating a first computer or a second computer of the multicomputer system included in the imaging modality.

FIG. 7 is a flow diagram which illustrates an exemplary flow process for operating the multicomputer modality in a workflow scenario. An exemplary workflow scenario with the multicomputer modality as described above may take place as follows. At step S700, it is assumed that an operator (technologist) would start (power ON) the modality at start an exam process. To that end, the operator would, at step S702, login into the modality's interface, for example provide credential as an authorized user of the modality. In the example provided above, where the RadPRO® 40 kW Digital Mobile X-ray system is used, the operator would login into modality 10 through the CXDI NE login screen. At step S704, the operator uses the toggle switch TSW to switch from the main computer to the second computer (slave computer) interface to access third party applications. For example, the operator clicks on a toggle switch labeled X-Ray/Workstation to access third party applications. The operator searches, for example, in a Cerner® application for a patient order (S706), and therein the operator can "Start" a patient's exam. Thereafter, at step S708, the operator may again use the toggle switch TSW, e.g., the operator clicks on the switch labeled X-Ray/Workstation to switch back to the main computer (first computer) to access the modality's application (e.g., CXDI NE application). Once the operator has access to the modality's application, the operator may activate the modality for examination procedure, by setting exam parameters and preparing a subject for examination (S710).

At step S712, continuing to use the modality's application (main computer interface), the operator proceed to perform an imaging operation. After selecting patient an exam type (body part protocol) is selected and the exam started. An imaging operation may require one or more images to be taken. For example, in an X-ray imaging modality, after one or more exposures are taken, and if everything looks acceptable on the mobile the exam is ended. Once the exam or imaging operation is completed, at step S714, the operator may once more use the toggle switch TSW, for example the operator clicks on a switch labeled EMR/PACS to access the third party applications interface on the slave computer.

Once back in the slave computer, the operator accesses third party applications. For example, the operator may login into a healthcare facility's Agfa Impax PACS. Therein, the operator performs quality control of the exam just completed, by evaluating the images sent to PACS. The images are transferred to PACS from the first or main computer during DICOM transmission after the end of a study. The technician then does a Q.C. of the images ensuring all images have been successfully sent and all images have sufficient image quality. If all the images have been sent and all images look good (YES at S718), the operator proceeds to end the exam (S720). If the exam results are not satisfactory (NO at S718), the operator would seamlessly switch back to the modality's application (main computer). Therefore, the flow process returns to S708, and the operator would repeat steps S708 to S710 until satisfactory exam results are obtained.

If all the images have been sent and all images look good the operator may safely end the exam. Then the operator would log out from one third party application and a second third party application, if necessary (S722). For example, the operator may log out of Agfa Impax and log into the Cerner application, where the patient is searched for and the study is closed. Thereafter, the operator may switch back to the modality's application (S724) to safely shutdown the imaging modality (S726) using the system software shutdown routine. Alternatively, the operator may choose to use the hardware shutdown routine directly at step S722, by operating a power OFF button on the imaging modality. In this case, the power control circuit 260 will ensure a safe shutdown sequence in accordance with the flow of FIG. 5B.

Some of the advantages of implementing an imaging modality with plural computer in the manner described above include, but are not limited to, (a) the ability to maintain the imaging modality in its original government-approved state, which ensures system performance and compliance, (b) the ability to run required third party software application without interfering with the modality's original software running in the modality's master computer, (c) the operating system of the second computer can be independent from that used in the modality's computer, indeed even open source operating systems or software applications can be freely installed in the slave computer, (d) the ability to install and run third party applications directly from the imaging modality is seen as an important aspect for vendors of third party applications which run on legacy platforms no longer supported by newer operating systems, (d) the ability to run third party applications directly from the imaging modality will contribute to streamline the workflow of medical imaging, will increase the productivity of imaging technicians, and alleviate patients of unnecessary burdens.

While the present application has been described with reference to exemplary embodiments, persons having ordinary skill in the art will appreciate that many variations are possible within the scope of the examples described herein. Thus, should be understood that structural and functional modifications may be made without departing from the scope of the following claims to which it should be accorded the broadest reasonable interpretation.

What is claimed is:

1. A radiographic imaging modality, comprising:
a first computer configured to control operations of the radiographic imaging modality;
a second computer configured to control communications of the radiographic imaging modality with an apparatus external to the radiographic imaging modality;
a computer select circuit connected to a manually operable switch and configured to allow an operator to select whether to operate the first computer or the second computer by manually operating the manually operable switch;
a single power supply unit configured to supply operating power to the radiographic imaging modality including the first computer and the second computer; and
a power control circuit connected to the single power supply unit, to the first computer, and to the second computer, and configured to detect whether the radiographic imaging modality receives a turn ON request or a turn OFF request,
wherein the power control circuit, responsive to detecting that the radiographic imaging modality receives a turn ON or turn OFF request, outputs a first trigger signal to activate or deactivate flow of power supply to the first computer, and outputs a second trigger signal to activate or deactivate flow of power supply to the second computer.

2. The radiographic imaging modality according to claim 1, wherein the power control circuit is configured to implement a time-controlled power-up sequence of the first and second computers, and
wherein, in the case in which the radiographic imaging modality receives a turn ON request, the power control circuit outputs the first trigger signal to activate the flow of power supply to turn the first computer ON and, after a predetermined time delay, outputs the second trigger signal to activate the flow of power supply to turn the second computer ON.

3. The radiographic imaging modality according to claim 2, wherein, after outputting the first and second trigger signals, the power control circuit locks operations of the radiographic imaging modality for a predetermined period of time until the first computer and the second computer have completely booted onto respective operating systems.

4. The radiographic imaging modality according to claim 1, wherein the power control circuit is configured to implement a time-controlled power-down sequence of the second and first computers, wherein, in a case in which the radiographic imaging modality receives a turn OFF request, the first computer sends the turn OFF request to the second computer via a direct communication link provided therebetween, the power control circuit outputs the second trigger signal to deactivate the flow of power supply to turn the second computer OFF and outputs the first trigger signal to deactivate the flow of power supply to turn the first computer OFF, and wherein the power control circuit delays a turn OFF operation of the first computer until the second computer completes a power-down routine.

5. The radiographic imaging modality according to claim 4, wherein the power control circuit locks operations of the radiographic imaging modality for a predetermined period of time until the first computer and the second computer have completely turned OFF from their respective operating systems; and wherein, after the first computer and the second computer have completely turned OFF, the power control circuit outputs a shutdown signal to the single power supply unit to turn the radiographic imaging modality OFF.

6. The radiographic imaging modality according to claim 4, wherein the turn OFF request is provided by manual operation of a power OFF switch of the radiographic imaging modality.

7. The radiographic imaging modality according to claim 4, wherein the turn OFF request is provided by a shutdown command through a software application of the first computer.

8. The radiographic imaging modality according to claim 1, wherein the first computer controls radiographic imaging operations of the radiographic imaging modality to acquire a radiographic image, and the second computer controls third party applications not affecting the radiographic imaging operations of the radiographic imaging modality to transmit the acquired radiographic image to the external apparatus.

9. The radiographic imaging modality according to claim 1, wherein, responsive to detecting that the radiographic imaging modality receives a turn ON request, the power control circuit outputs the first trigger signal to activate the flow of power supply to the first computer, and after a time delay outputs the second trigger signal to activate the flow of power supply to the second computer, so that the first computer and the second computer are turned ON in this order.

10. The radiographic imaging modality according to claim 1, wherein, responsive to detecting that the radiographic imaging modality receives a turn OFF request, the power control circuit outputs the second trigger signal to deactivate the flow of power supply to the second computer, and after a time delay outputs the first trigger signal to deactivate the flow of power supply to the first computer, so that the second computer and the first computer are turned OFF in this order.

11. The radiographic imaging modality according to claim 1, wherein the radiographic imaging modality is a portable X-ray system, and wherein the single power supply unit continuously powers the power control circuit via a stand-by signal even when the imaging modality is in a stand-by state or in an OFF state.

12. The power control circuit according to claim 1, wherein the power control circuit continuously checks a status of power supply from the single power supply unit to the first and second computers.

13. A power control circuit operatively connected to a first computer and a second computer disposed within a radiographic imaging modality, wherein the first computer controls operations of the radiographic imaging modality, and the second computer controls communications of the radiographic imaging modality with an apparatus external to the radiographic imaging modality, and wherein the power control circuit controls flow of voltage supply from a single voltage supply unit to the first and second computer, the power control circuit comprising:

a voltage input connection configured to receive operating voltage from the single voltage supply unit;

a first terminal connected to the first computer; and a second terminal connected to the second computer, wherein the power control circuit is configured to detect whether the radiographic imaging modality receives a turn ON request or a turn OFF request, and wherein the power control circuit, responsive to detecting that the radiographic imaging modality receives a turn ON or turn OFF request, outputs a first trigger signal to activate or deactivate the flow of voltage supply to the first computer, and outputs a second trigger signal to activate or deactivate the flow of voltage supply to the second computer.

14. The power control circuit according to claim 13, wherein the power control circuit is configured to implement a time-controlled power-up sequence of the first and second computers, and wherein, in a case in which the power control circuit detects that the radiographic imaging modality receives a turn OFF request, the power control circuit outputs the first trigger signal to activate the flow of voltage supply to turn the first computer ON and, after a predetermined time delay outputs the second trigger signal to activate the flow of voltage supply to turn the second computer ON.

15. The power control circuit according to claim 13, wherein, after outputting the first and second trigger signals, the power control circuit locks operations of the radiographic imaging modality for a predetermined period of time until the first computer and the second computer have completely booted onto respective operating systems.

16. The power control circuit according to claim 13, wherein the power control circuit is configured to implement a time-controlled power-down sequence of the second and first computers, wherein, in a case in which the radiographic imaging modality receives a turn OFF request, the first computer sends the turn OFF request to the second computer via a direct communication link provided therebetween, and the power control circuit outputs the second trigger signal to deactivate the flow of voltage supply to turn the second computer OFF and outputs the first trigger signal to deactivate flow of voltage supply to turn the first computer OFF, and wherein the power control circuit delays a turn OFF operation of the first computer until the second computer completes a power-down routine.

17. The power control circuit according to claim 16, wherein the power control circuit locks operations of the radiographic imaging modality for a predetermined period of time until the first computer and the second computer have completely turned OFF from their respective operating systems, and wherein, after the first computer and the second computer have completely turned OFF, the power control circuit outputs a shutdown signal to the single voltage supply unit to turn the radiographic imaging modality OFF.

18. The power control circuit according to claim 16, wherein the turn OFF request is provided by manual operation of a power OFF switch of the radiographic imaging modality.

19. The power control circuit according to claim 16, wherein the turn OFF request is provided by a shutdown command through a software application of the first computer.

20. A power control circuit operatively connected to a first computer and a second computer disposed within a radiographic imaging modality, wherein the first computer controls operations of the radiographic imaging modality, and the second computer controls communications of the radiographic imaging modality with an apparatus external to the radiographic imaging modality, and wherein the power control circuit controls flow of voltage supply from a single voltage supply unit to the first and second computer, the power control circuit comprising:

a voltage input connection configured to receive operating voltage from the voltage supply unit;

a first programmable port connected to the first computer; and a second programmable port connected to the second computer, wherein the power control circuit is configured to continuously monitor a voltage supply status of the first computer and the second computer, wherein, responsive to detecting that the first computer receives a turn ON request, the power control circuit outputs a first trigger signal to the voltage supply unit to activate the flow of voltage supply to the first computer, and after a predetermined delay outputs a second trigger signal to the voltage supply unit to activate the flow of voltage supply to the second computer, wherein, responsive to detecting that the first computer receives a turn OFF request, the first computer sends the turn OFF request to the second computer via a direct communication link provided therebetween, the power control circuit outputs a first trigger signal to the voltage supply unit to deactivate the flow of voltage supply to the second computer, and after a predetermined delay outputs a second trigger signal to the voltage supply unit to deactivate the flow of voltage supply to the first computer, and wherein, after the flow of voltage supply from the voltage supply unit to both the first computer and the second computer has been deactivated, the power control circuit outputs a shutdown signal to the voltage supply unit to turn the radiographic imaging modality OFF.

\* \* \* \* \*